US011266324B2

(12) United States Patent
Polimeni et al.

(10) Patent No.: US 11,266,324 B2
(45) Date of Patent: Mar. 8, 2022

(54) SYSTEM AND METHODS FOR FAST MULTI-CONTRAST MAGNETIC RESONANCE IMAGING

(71) Applicant: THE GENERAL HOSPITAL CORPORATION, Boston, MA (US)

(72) Inventors: Jonathan Polimeni, Cambridge, MA (US); Andre Van Der Kouwe, Woburn, MA (US); Matthew Tisdall, Somerville, MA (US); Bruce Fischl, Cambridge, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 1161 days.

(21) Appl. No.: 15/305,515

(22) PCT Filed: Apr. 24, 2015

(86) PCT No.: PCT/US2015/027450
§ 371 (c)(1),
(2) Date: Oct. 20, 2016

(87) PCT Pub. No.: WO2015/164701
PCT Pub. Date: Oct. 29, 2015

(65) Prior Publication Data
US 2017/0035321 A1 Feb. 9, 2017

Related U.S. Application Data

(60) Provisional application No. 61/983,700, filed on Apr. 24, 2014.

(51) Int. Cl.
A61B 5/055 (2006.01)
G01R 33/50 (2006.01)
(Continued)

(52) U.S. Cl.
CPC .............. *A61B 5/055* (2013.01); *G01R 33/50* (2013.01); *G01R 33/5602* (2013.01); *G01R 33/5611* (2013.01); *G01R 33/58* (2013.01)

(58) Field of Classification Search
CPC .... A61B 5/055; G01R 33/50; G01R 33/5602; G01R 33/5611; G01R 33/58
See application file for complete search history.

(56) References Cited

U.S. PATENT DOCUMENTS 5,245,282 A 9/1993 Mugler
7,602,179 B2 10/2009 Van Der Kouwe
(Continued)

OTHER PUBLICATIONS

Marques et al. "MP2RAGE, a self bias-field corrected sequence for improved segmentation and T1-mapping at high field". NeuroImage 49 (2010) 1271-1281 (Year: 2010).*
(Continued)

Primary Examiner — Christopher Koharski
Assistant Examiner — Milton Truong
(74) Attorney, Agent, or Firm — Quarles & Brady LLP

(57) ABSTRACT

Systems and methods for performing fast multi-contrast magnetic resonance imaging ("MRI") are provided. In general, data are acquired from both multiple echo times ("TEs") and at multiple effective inversion times ("TIs"). Following the application of a magnetization preparation radio frequency ("RF") pulse, a plurality of different multi-echo acquisitions are performed, thereby acquiring data from multiple different TEs during different portions of the longitudinal magnetization recovery curve. Data acquisition in these inner encoding loops (i.e., during each multi-echo acquisition) can be accelerated to efficiently provide for the acquisition of multiple contrasts in the time normally required to acquire a single contrast.

19 Claims, 2 Drawing Sheets

(51) Int. Cl.
   *G01R 33/56*   (2006.01)
   *G01R 33/561*   (2006.01)
   *G01R 33/58*   (2006.01)

(56) References Cited

U.S. PATENT DOCUMENTS

| | | | |
|---|---|---|---|
| 2004/0169512 A1* | 9/2004 | Jara | G01R 33/50 |
| | | | 324/309 |
| 2004/0263169 A1* | 12/2004 | Mitchell | G01R 33/56 |
| | | | 324/309 |
| 2008/0012563 A1* | 1/2008 | Weiss | G01R 33/4824 |
| | | | 324/307 |
| 2008/0108894 A1* | 5/2008 | Elgavish | G06T 7/0012 |
| | | | 600/420 |
| 2008/0116891 A1* | 5/2008 | van der Kouwe | G01R 33/561 |
| | | | 324/312 |
| 2008/0278160 A1 | 11/2008 | Griswold | |
| 2011/0084693 A1* | 4/2011 | Kholmovski | G01R 33/5611 |
| | | | 324/310 |
| 2012/0013336 A1* | 1/2012 | Hetzer | G01R 33/485 |
| | | | 324/309 |
| 2012/0179028 A1 | 7/2012 | Caravan | |
| 2012/0232378 A1 | 9/2012 | Messroghli | |
| 2012/0286783 A1* | 11/2012 | Constable | G01R 33/5611 |
| | | | 324/309 |
| 2013/0099784 A1* | 4/2013 | Setsompop | G01R 33/54 |
| | | | 324/309 |
| 2013/0274592 A1* | 10/2013 | Shin | A61B 5/055 |
| | | | 600/420 |
| 2014/0292330 A1* | 10/2014 | Gulani | G01R 33/4822 |
| | | | 324/309 |

OTHER PUBLICATIONS

Clarke, G.D "Optimizing MR Imaging Procedures: The Physicist as a Consultant". Annual Meeting of American Association of Physicists in Medicine, Seattle, Washington (2005) (Year: 2005).*
Deoni, SCL. "Quantitative relaxometry of the brain." Topics in magnetic resonance imaging: TMRI 21.2 (2010): 101.
Fischl, B., et al. "Sequence-independent segmentation of magnetic resonance images." Neuroimage 23 (2004): S69-S84.
International Searching Authority, International Search Report and Written Opinion for application PCT/US2015/027450, dated Jul. 22, 2015, 11 pages.
Mugler III, John P., et al. "Rapid three-dimensional T1-weighted MR imaging with the MP-RAGE sequence." Journal of Magnetic Resonance Imaging 1.5 (1991): 561-567.

* cited by examiner

SYSTEM AND METHODS FOR FAST MULTI-CONTRAST MAGNETIC RESONANCE IMAGING

CROSS-REFERENCE TO RELATED APPLICATIONS

This application, represents the U.S. National Stage of International Application No. PCT/US2015/027450, filed on Apr. 24, 2015 which claims the benefit of U.S. Provisional Patent Application Ser. No. 61/983,700, filed on Apr. 24, 2014, both of which are incorporated herein by reference for all purposes.

STATEMENT REGARDING FEDERALLY SPONSORED RESEARCH

This invention was made with government support under R21 AG046657, MH096559, and HD071664 awarded by the National Institutes of Health. The government has certain rights in the invention.

BACKGROUND

The present disclosure relates to systems and methods for magnetic resonance imaging ("MRI"). More particularly, the present disclosure relates to systems and methods for directing an MRI system to acquire images with multiple different image contrasts in the time normally required to acquire images with a single image contrast.

In conventional anatomical magnetic resonance imaging, the imaging protocol is typically optimized for a specific tissue contrast, such that the data is acquired in a fixed amount of time. It is possible to collect multiple contrasts (e.g., T1 contrast and T2* contrast) in the same fixed amount of time; however, doing so will reduce image signal-to-noise ratio per contrast.

The magnetization-prepared rapid gradient echo ("MPRAGE") technique is a commonly used MRI acquisition method applied in anatomical imaging. In MPRAGE, a number of partition-encoded k-space lines are read out after a single magnetization preparation pulse, such that a set of partition-encoded k-space lines are acquired during each inversion recovery period. This technique is typically used to achieve uniform T1-weighting over the object being imaged and can achieve high nominal resolutions of about 1 mm isotropic in under 10 minutes of acquisition. When receive coil arrays are available, it is common to reduce this acquisition time substantially by using accelerated parallel imaging techniques that skip a subset of the inversion recoveries during the image encoding, and this missing data can be estimated during image reconstruction with standard parallel imaging methods such as GRAPPA.

Despite the advances in parallel imaging techniques, the currently-available techniques for anatomical imaging still face the difficulties in acquiring multiple different image contrasts in a clinically feasible amount of time.

SUMMARY

The present disclosure provides systems and methods that overcome the aforementioned drawbacks by using a series of images that depict different image contrasts using a magnetic resonance imaging ("MRI") system. The MRI system is directed to acquire multi-contrast data by performing a pulse sequence that includes a variety of steps.

In accordance with one example, the pulse sequence may include (i) applying a magnetization preparation radio frequency (RF) pulse to create magnetization-prepared longitudinal magnetization and (ii) performing a multi-echo acquisition to acquire data from multiple different echo times during a period of time in which the magnetization-prepared longitudinal magnetization is recovering to equilibrium. The pulse sequence may also include (iii) repeating step (ii) a plurality of times to acquire data from the multiple different echo times during different periods of time in which the magnetization-prepared longitudinal magnetization is recovering to equilibrium to achieve multiple different effective inversion times. The data acquired in steps (ii) and (iii) collectively form the multi-contrast data. The method also includes reconstructing a series of images that depict different image contrasts from the multi-contrast data.

In accordance with another aspect of the disclosure, a magnetic resonance imaging (MRI) system is provided that includes a magnet system configured to generate a static magnetic field about at least a portion of a subject arranged in the MRI system and a gradient coil system configured to establish at least one magnetic gradient field with respect to the static magnetic field. The MRI system also includes a radio frequency (RF) system configured to deliver excitation pulses to the subject and acquire data from the subject and a computer system. The computer system is programmed to control the RF system to applying a magnetization preparation RF pulse to create magnetization-prepared longitudinal magnetization and control the gradient coil system and the RF system to acquire accelerated imaging data while the magnetization-prepared longitudinal magnetization is recovering to equilibrium by skipping a subset of phase-encoding or partition-encoding steps. The computer system is also programmed to control the gradient coil system and the RF system to repeatedly acquire the accelerated imaging data for each phase encoding, or partition encoding, to acquire a multi-contrast image dataset and reconstruct a series of images that depict different image contrasts from the multi-contrast dataset.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
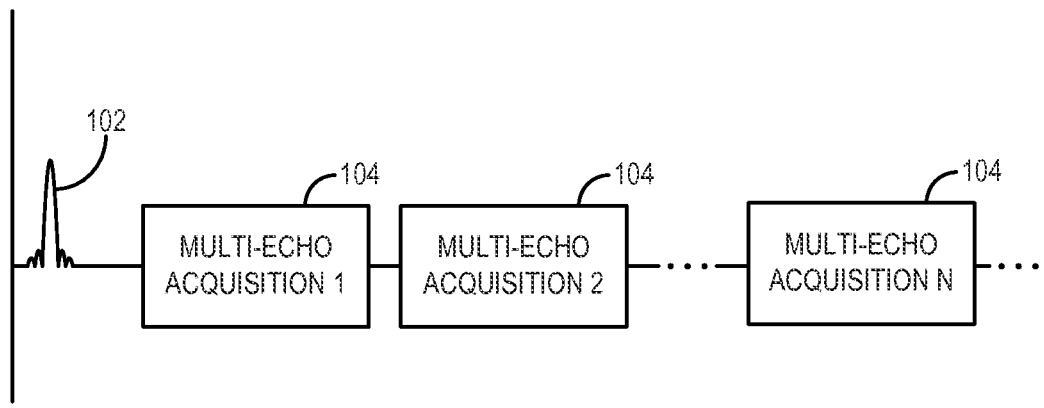
FIG. 1 is a schematic representation of a pulse sequence that can be used to implement systems and methods in accordance with the present disclosure.

Systems and method are described herein for performing fast multi-contrast magnetic resonance imaging ("MRI"). In general, data are acquired from both multiple echo times ("TEs") and multiple effective inversion times ("TIs"). During each effective TI period, a plurality of different multi-echo acquisitions are performed, thereby acquiring data from multiple different TEs during different portions of the longitudinal magnetization recovery curve. Data acquisition in these inner encoding loops (i.e., during different portions of the longitudinal magnetization recovery curve) efficiently provides for the acquisition of multiple contrasts in the time normally required to acquire a single contrast.

The systems and methods of the present disclosure are not only capable of acquiring multiple TEs or multiple effective TIs, but enable both multiple TEs and effective TIs in a single acquisition. In addition, the systems and methods of the present disclosure can be used to support an arbitrary number of TIs and TEs. With this acceleration, these multiple different contrasts can be collected in the same amount of time as a conventional acquisition. This increased number of contrasts facilitates quantification of parameters such as proton density ("PD"), T1 and T2* by fitting parametric models to the acquired images.

In some configurations, the systems and methods of the present disclosure may use a magnetization-prepared rapid gradient echo ("MP-RAGE") technique that acquires data from multiple TEs and multiple effective TIs in the time of one acquisition by increasing imaging bandwidth and by accelerating in the inner encoding loop (i.e., during the inversion recovery). As will be described below, the resulting multiple image contrasts can be used separately to generate multi-spectral data (e.g., for segmentation); can be combined to generate a highly-accurate image of a single, weighted contrast; or can be used in a fitting procedure to calculate T1 and T2* values for a sequence-independent parametric map of the tissue for either direct segmentation or for synthesizing arbitrary image contrasts.

Generally speaking, the parallel imaging techniques applied to accelerate the data acquisition during the inner encoding loop are not applied to speed up the acquisition time, but to improve image quality and to enable quantitative magnetic resonance parameter mapping. For instance, rather than skipping a subset of inversion recoveries, the systems and methods of the present disclosure accelerate during the inversion recovery by skipping a subset of phase-encoding or partition-encoding steps. The missing data can then be estimated using standard parallel imaging methods, such as GRAPPA.

By shortening the time required to acquire the image data during the inversion recovery, multiple independent acquisitions can be performed during a single inversion recovery. These multiple independent acquisitions produce multiple images having different effective TIs and, therefore, different levels of T1-weighted tissue contrast. This acquisition can be referred to as an "MPx-RAGE" acquisition because a variable number of gradient echo readouts are acquired during each inversion recovery following the magnetization preparation pulse. Note that the acceleration during the inversion recovery is compatible with conventional achieved acceleration by skipping a subset of inversion recoveries to reduce the total acquisition time.

This multiple-TI approach can also be combined with a multi-echo acquisition, such as a multi-echo MPRAGE ("ME-MPRAGE") method, such as described in U.S. Pat. No. 7,602,179, which is incorporated herein by reference in its entirety, to generate multiple TEs as well. By acquiring data at multiple different TEs, multiple levels of T2* contrast can be obtained along with the multiple levels of T1 contrast. The imaging procedure described here can thus be referred to as an ME-MPx-RAGE acquisition, and can efficiently produce multiple images of varying T1 and T2* contrast in the same amount of time required by a conventional acquisition to acquire a single image with a single contrast.

The conventional ME-MPRAGE method acquires multiple echoes by increasing the readout bandwidth in order to shorten the time required for each readout line. This has the effect of reducing the vulnerability to geometric distortion caused by macroscopic magnetic susceptibility gradients in the object and other off-resonance effects. Similarly, the multiple effective inversion times achieved by the MPx-RAGE method are also enabled by shortening the time required for each inversion recovery acquisition, but this is accomplished by accelerated parallel imaging techniques. This reduced acquisition time similarly provides a benefit in image quality by reducing the vulnerability to blurring effects caused by the T1 recovery during the acquisition window in each inversion recovery. Therefore, these time-shortening techniques enable more contrasts to be acquired in a given image acquisition, while reducing image artifacts.

Referring now to FIG. 1, an example pulse sequence diagram for a multi-inversion-recovery, multi-echo magnetization-prepared rapid gradient echo ("ME-MPx-RAGE") is illustrated. In general, the pulse sequence includes a magnetization preparation pulse 102 followed by a plurality of multi-echo acquisitions 104 that are performed as the longitudinal magnetization recovers back to equilibrium following the application of the magnetization preparation pulse 102. By way of example, the magnetization preparation RF pulse 102 can include an inversion recovery RF pulse.

Figure 2:
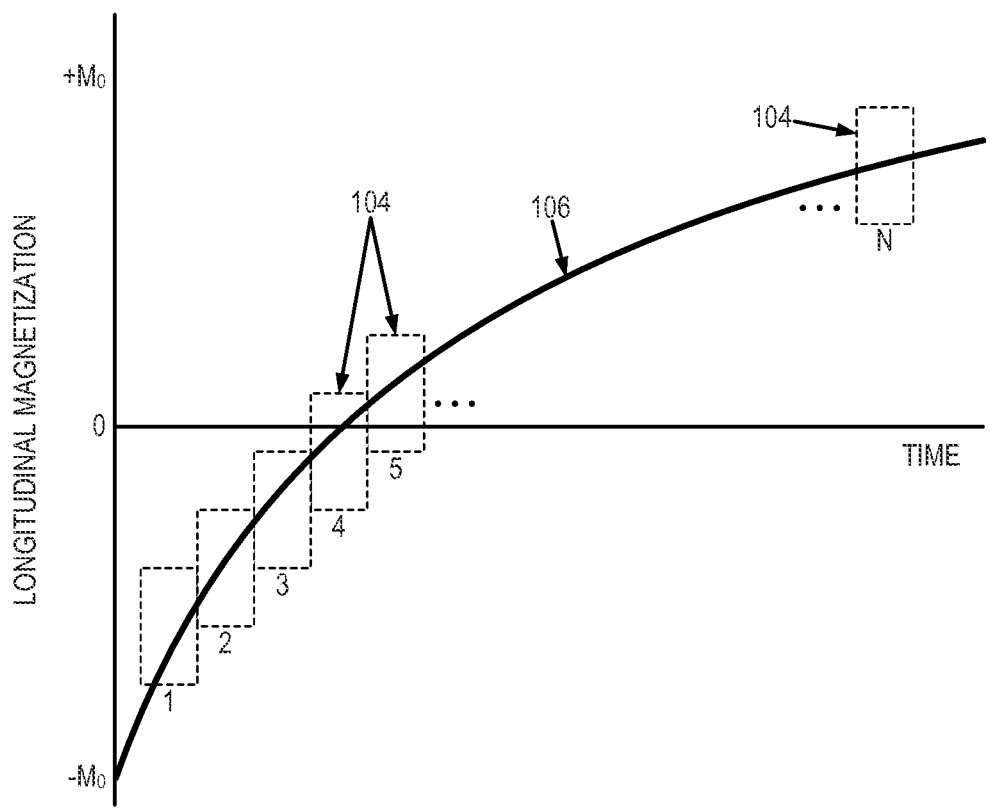
FIG. 2 is an illustration of how the pulse sequence of FIG. 1 samples data during multiple different periods of time during which longitudinal magnetization is recovering to equilibrium.

As illustrated in FIG. 2, each multi-echo acquisition 104 samples a different portion of the longitudinal magnetization recovery curve 106 as the magnetization recovers back to equilibrium following application of the magnetization preparation RF pulse 102. For instance, each multi-echo acquisition 104 can sample blocks of the longitudinal magnetization recovery curve 106, where each block has a different effective inversion time ("TI") (e.g., TI=1000, 1500, 2000, 2500 ms). As stated above, within each of these blocks, data is acquired from multiple different echo times (e.g., TE=2, 4, 6, 8 ms).

In some implementations, each multi-echo acquisition 104 includes sampling multiple gradient echoes. For instance, each multi-echo acquisition can include applying a series of RF excitation pulses, each producing a series of gradient-recalled echo signals. An example of such a multi-echo acquisition scheme is described in U.S. Pat. No. 7,602,179.

In some configurations, each multi-echo acquisition is phase encoded (for 2D acquisitions) or partition encoded (for 3D acquisitions) only once. As a result, the multi-echo acquisition is repeated once for each phase encoding, or partition encoding, value needed to acquire a complete k-space image data set. In these examples, each multi-echo acquisition is repeated a number of times equal to the number of phase-encoding or partition-encoding steps. At each phase encoding or partition encoding step, a number of echoes (e.g., from 1 to 12 or more) are generated.

In some configurations, each multi-echo acquisition 104 implements an accelerated data acquisition scheme, in which a number of phase-encoding or partition-encoding steps are skipped. This acquisition scheme results in the acquired data being undersampled along the phase-encoding or partition-encoding direction, respectively. It is noted that this accelerated data acquisition scheme is performed to accelerate data acquisition in each effective TI block (i.e., inner loop acceleration). Thus, for example, the k-space lines in a given plane in k-space are undersampled during each multi-echo acquisition. With this acceleration, it is possible to collect a given k-space plane repeatedly at several effective inversion times after a single inversion recovery pulse in the time normally required to collect data at a single inversion time. In some configurations, the inner-loop acceleration is compatible with an integrated auto-calibration acquisition, such as may be used for GRAPPA training. In these instances, the acquisition of fully-sampled auto-calibration data for GRAPPA kernel training can be integrated into each multi-echo acquisition.

In some configurations, this auto-calibration data can be acquired to exhibit the same image contrast as the accelerated data through a variable-density sampling approach, in which the center of k-space is fully sampled during the accelerated image encoding within each inversion recovery. Alternatively, the auto-calibration may be acquired separately from the image data. The GRAPPA method is somewhat insensitive to differences in image contrast between auto-calibration data and the accelerated data, and therefore the contrast of the separately acquired auto-calibration data need not match the contrast of the accelerated data. For instance, magnetization preparation can be omitted from a separate auto-calibration acquisition to improve the time efficiency of the auto-calibration acquisition.

As one non-limiting example, the ME-MPx-RAGE pulse sequence for a three-dimensional acquisition can include four echo times (e.g., TE=2/4/6/8 ms) and three effective inversion times for a total of twelve different contrasts. This example acquisition can include obtaining a voxel volume of 224×224×192 voxels (frequency encodings x phase encodings x partition encodings) acquired for each contrast. With an acceleration factor of R=2 in the phase-encoding direction (to reduce the overall scan time) and an acceleration factor of R=3 in the partition-encoding direction (to fit all effective inversion times within a single inversion recovery), each multi-echo acquisition 104 would include four echoes repeated for all 192/3=64 partition-encoding steps. This multi-echo acquisition would be repeated N=3 times to generate three effective inversion times during a single inversion recovery. In the outer loop, the magnetization preparation and the multi-echo time, multi-inversion time acquisition would be repeated 224/2=112 times.

The data acquired using the ME-MPx-RAGE acquisition scheme described above can be used to reconstruct multiple different images with multiple different image contrasts. In some configurations, these resulting multiple image contrasts can be used to generate multi-spectral data (e.g., for segmentation).

The associated penalty of these time-shortening techniques is that signal-to-noise ratio is also reduced since there is less time-averaging of thermal noise and thus less noise cancellation in the measurement. This intrinsic loss in signal-to-noise ratio can be largely recovered by averaging or combining the multiple independent images (each with a distinct contrast). Thus, in some configurations, the multiple images can be used to generate a highly-accurate image of a single, weighted contrast. This combination has the effect of cancelling uncorrelated noise between the individual images. While this combination step removes the benefit of having efficiently acquired multiple images of various T1 and T2* contrasts in a short amount of time, it provides a single image with far less distortion and blurring than a conventional image with comparable signal-to-noise ratio and is, therefore, a significant benefit—especially for morphometric applications.

In some other configurations, the multiple images with differing image contrast can be used to calculate T1 and T2* values for a sequence-independent parametric map of the tissue for either direct segmentation or for synthesizing arbitrary image contrasts. For instance, these, or other, magnetic resonance parameters can be calculated by fitting canonical models of signal decay and recovery to the images. Because these models are nonlinear, accurate parametric fitting requires multiple measurements for each unknown parameter value, and the images acquired with the ME-MPx-RAGE acquisition provide a sufficient number of measurements for these fits. The resulting quantitative T1 and T2* maps have the advantage of being robust to changes in the pulse sequence parameters or imaging hardware, and can therefore be used with automatic segmentation software for accurate tissue segmentation and identification.

Once parametric maps have been calculated, it is also possible to synthesize images corresponding to other pulse sequences or protocols to generate any desired synthetic image contrast. Because these fitting procedures typically assume that every image voxel was acquired with a single TI time, which is not the case since the acquisition duration during the inversion recovery is multiple seconds long, the acceleration during the inversion recovery used in MPx-RAGE compresses the acquisition time such that the assumption of a single TI time holds much better than in the conventional case. As a result, the form of acceleration proposed in this disclosure can actually improve the quantitative accuracy of the T1 fits.

Figure 3:
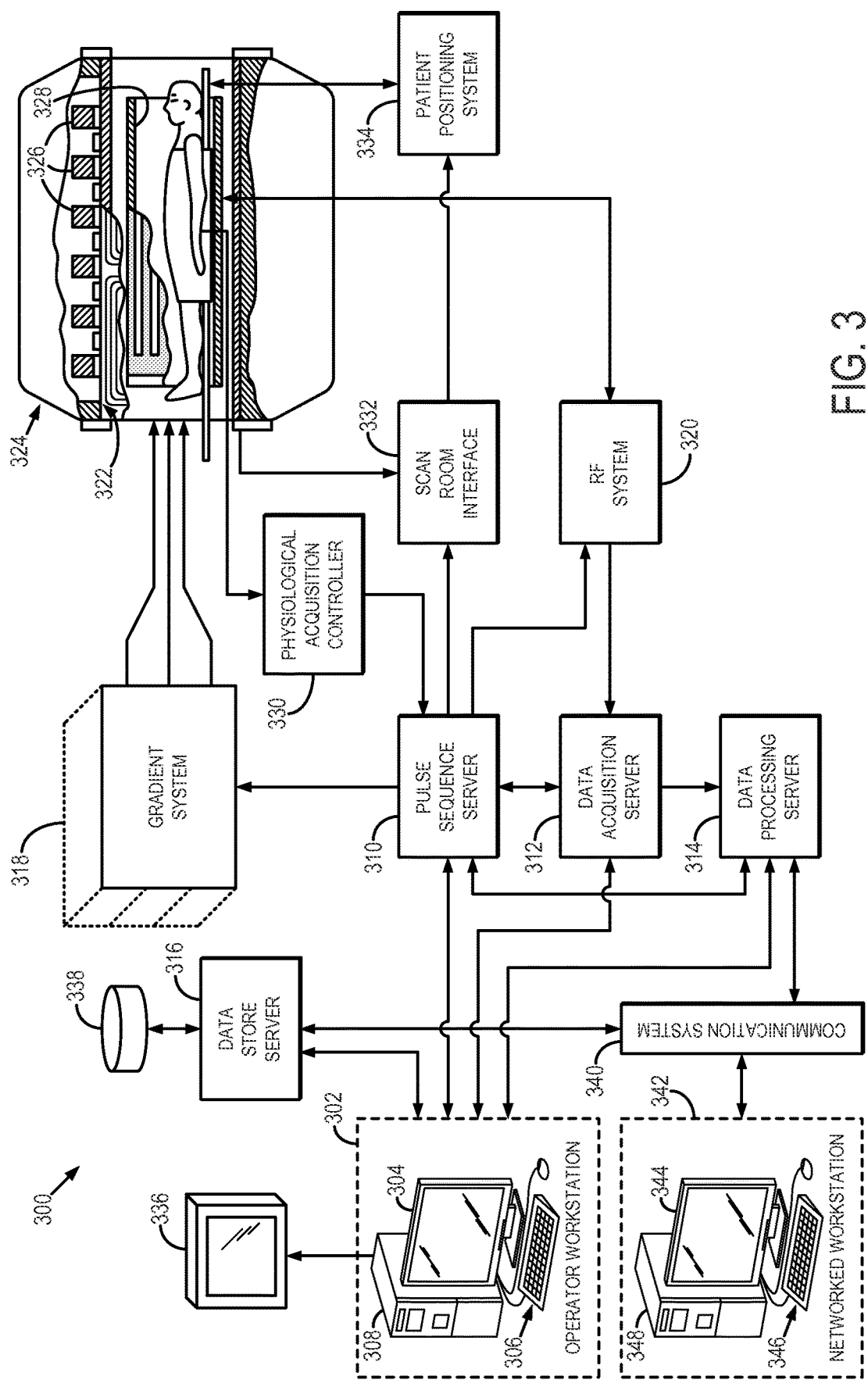
FIG. 3 is a block diagram of an example of a magnetic resonance imaging ("MRI") system that can be used to carry out the pulse sequence of FIG. 1.

Referring particularly now to FIG. 3, an example of a magnetic resonance imaging ("MRI") system 300 is illustrated. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing a series of images that depict different image contrasts using a magnetic resonance imaging (MRI) system, steps of the method comprising:

(a) directing the MM system to acquire multi-contrast data from a subject by performing a pulse sequence that includes:
  (i) applying a magnetization preparation radio frequency (RF) pulse to create magnetization-prepared longitudinal magnetization;
  (ii) performing a multi-echo acquisition to acquire data from multiple different echo times during a period of time in which the magnetization-prepared longitudinal magnetization is recovering along a continuously increasing recovery curve to equilibrium;
  (iii) repeating step (ii) a plurality of times to acquire data from the multiple different echo times during different periods of time in which the magnetization-prepared longitudinal magnetization is recovering to equilibrium to achieve multiple different effective inversion times;
  wherein the data acquired in steps (ii) and (iii) collectively form the multi-contrast data; and
(b) reconstructing a series of images that depict different image contrasts from the multi-contrast data.

2. The method as recited in claim 1, wherein the multi-echo acquisition performed in step (ii) implements an accelerated multi-echo data acquisition scheme in which data are undersampled along at least one direction ink-space.

3. The method as recited in claim 2, wherein the accelerated multi-echo acquisition is accelerated by undersampling along a direction in a plane of k-space.

4. The method as recited in claim 3, wherein the accelerated multi-echo acquisition undersamples k-space along a partition-encoding direction.

5. The method as recited in claim 4, further comprising acquiring calibration data during step (a), such that the calibration data and multi-contrast data have matching image contrasts.

6. The method as recited in claim 4, further comprising directing the MM system to acquire calibration data from the subject using a different pulse sequence than the pulse sequence performed in step (a).

7. The method as recited in claim 1, wherein the magnetization preparation RF pulse is an inversion recovery RF pulse.

8. The method as recited in claim 1, further comprising generating a segmented image of the subject based on the reconstructed series of images that depict different image contrasts.

9. The method as recited in claim 1, further comprising producing a parametric map that depicts a magnetic resonance parameter based on the reconstructed series of images that depict different image contrasts.

10. The method as recited in claim 9, wherein the parametric map is produced by fitting the reconstructed series of images that depict different image contrasts to a magnetic resonance signal model.

11. The method as recited in claim 9, wherein the magnetic resonance parameter is at least one of proton density (PD), longitudinal relaxation time (T1), and apparent transverse relaxation time (T2*).

12. The method as recited in claim 9, further comprising producing a synthesized image based on the parametric map and the reconstructed series of images that depict different image contrasts, the synthesized image depicting an image contrast not contained in the reconstructed series of images that depict different image contrasts.

13. The method as recited in claim 9, further comprising generating a segmented image of the subject based on the parametric map and the reconstructed series of images that depict different image contrasts.

14. A magnetic resonance imaging (MRI) system, comprising:
  a magnet system configured to generate a static magnetic field about at least a portion of a subject arranged in the MRI system;
  a gradient coil system configured to establish at least one magnetic gradient field with respect to the static magnetic field;
  a radio frequency (RF) system configured to deliver excitation pulses to the subject and acquire data from the subject;
  a computer system programmed to:
    control the RF system to applying a magnetization preparation RF pulse to create magnetization-prepared longitudinal magnetization;
    control the gradient coil system and the RF system to acquire accelerated imaging data while the magnetization-prepared longitudinal magnetization is recovering along a continuously increasing recovery curve to equilibrium by skipping a subset of phase-encoding or partition-encoding steps;
    control the gradient coil system and the RF system to repeatedly acquire the accelerated imaging data for each phase encoding, or partition encoding, to acquire a multi-contrast image dataset; and
    reconstruct a series of images that depict different image contrasts from the multi-contrast dataset, wherein the multi-contrast dataset includes data that spans both multiple echo times ("TEs") and multiple effective inversion times ("TIs").

15. The system as recited in claim 14, wherein the computer system is configured to estimate data missing in the accelerated imaging data using parallel imaging methods.

16. The system as recited in claim 14, wherein the computer system is further configured to control the gradient coil system and the RF system to acquire calibration data, such that the calibration data and multi-contrast data have matching image contrasts.

17. The system as recited in claim 16, wherein the computer system is further configured to use the calibration data in a parallel imaging reconstruction process to estimate data missing from the accelerated imaging data due to skipping the subset of phase encoding or partition-encoding steps.

18. The system as recited in claim 14, wherein the magnetization preparation RF pulse is an inversion recovery RF pulse.

19. The system as recited in claim 14, wherein the computer system is configured to produce a parametric map that depicts a magnetic resonance parameter based on the reconstructed series of images that depict different image contrasts.

* * * * *

UNITED STATES PATENT AND TRADEMARK OFFICE
CERTIFICATE OF CORRECTION

| | |
|---|---|
| PATENT NO. | : 11,266,324 B2 |
| APPLICATION NO. | : 15/305515 |
| DATED | : March 8, 2022 |
| INVENTOR(S) | : Jonathan Polimeni et al. |

It is certified that error appears in the above-identified patent and that said Letters Patent is hereby corrected as shown below:

In the Claims

Column 9, Claim 1, Line 1, "MM" should be --MRI--.

Column 9, Claim 6, Line 37, "MM" should be --MRI--.

Signed and Sealed this
Third Day of May, 2022

Katherine Kelly Vidal
*Director of the United States Patent and Trademark Office*